United States Patent [19]

Mizukawa

[11] Patent Number: 5,055,587
[45] Date of Patent: Oct. 8, 1991

[54] PROCESS FOR PREPARING 1H-PYRAZOLO-[5,1-C]-1,2,4-TRIAZOLE COMPOUNDS

[75] Inventor: Yuki Mizukawa, Ashigara, Japan

[73] Assignee: Fuji Photo Film Co., Ltd., Kanagawa, Japan

[21] Appl. No.: 323,963

[22] Filed: Mar. 15, 1989

[30] Foreign Application Priority Data

Mar. 15, 1988 [JP] Japan .................................. 63-61183

[51] Int. Cl.$^5$ .......................................... C07D 487/04
[52] U.S. Cl. .................................. 548/262.4; 546/271; 548/250; 548/252; 548/253; 548/254; 548/257; 548/260; 548/261; 548/159
[58] Field of Search ............ 548/262, 266, 362, 262.4, 548/250, 252, 253, 254, 257, 260, 261, 336, 327; 548/271

[56] References Cited

U.S. PATENT DOCUMENTS

| | | | |
|---|---|---|---|
| 3,725,067 | 4/1973 | Bailey et al. | 548/262 |
| 4,705,863 | 11/1987 | Sato et al. | 548/262 |
| 4,812,576 | 3/1989 | Wolff et al. | 548/262 |

OTHER PUBLICATIONS

Mizukara et al., "Preparation of 7-Cyano, etc.", CA 110:23896a (1989).

Primary Examiner—Mary C. Lee
Assistant Examiner—Patricia L. Morris
Attorney, Agent, or Firm—Birch, Stewart, Kolasch & Birch

[57] ABSTRACT

A process for preparing a 1H-pyrazolo[5,1-C]-1,2,4-triazole compound represented by the following general formula (I):

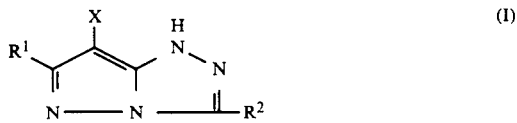

wherein $R^1$ represents a hydrogen atom or a substituent group, $R^2$ represents an alkyl group, an aryl group or a heterocyclic ring group, and X represents a hydrogen atom or a substituent group, which process comprises reacting either an imidic acid ester represented by the following general formula (II):

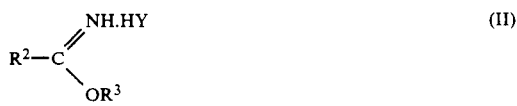

wherein $R^2$ is as defined above, $R^3$ represents an alkyl group, and Y represents an acid radical, or an orthoester represented by the following general formula (III):

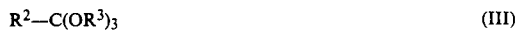

wherein $R^2$ and $R^3$ are as defined above, with a 5-hydroazino-1H-pyrazole compound represented by the following general formula (IV):

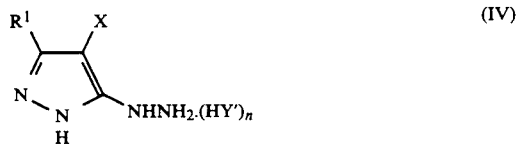

wherein $R^1$ and X are as defined above, Y' represents an acid radical, and n represents 0 or a positive integer necessary to neutralize the intramolecular electric charge.

19 Claims, No Drawings

PROCESS FOR PREPARING 1H-PYRAZOLO-[5,1-C]-1,2,4-TRIAZOLE COMPOUNDS

FIELD OF THE INVENTION

The present invention relates to a process for preparing 1H-pyrazolo[5,1,-c]-1,2,4-triazole compounds which are useful as couplers for silver halide color films.

BACKGROUND OF THE INVENTION

1H-Pyrazolo[5,1-c]-1,2,4-triazole compounds are useful compounds as magenta couplers for use in developing silver halide color films. Several methods of synthesizing compounds of this class are known. However, these known methods have various disadvantages.

One known method for synthesising 1H-pyrazolo[5,1,-c]-1,2,4-triazole compounds is described in U.S. Pat. No. 3,725,067, U.K. Patent No. 1,252,418 and in the "Journal of the Chemical Society", Perkin I,pp. 2047-2052 (1977). According to this method, a 5-hydrazino-1H-pyrazol-4-carboxylate compound is acylated to obtain a 5-acylhydrazino-1H-pyrazol-4-carboxylate compound, and then the resulting acylated compound is heated under reflux with benzene and phosphorous oxychloride for a relatively long time to thereby obtain a 1H-pyrazolo[5,1-c]-1,2,4-triazole compound.

However, the above-mentioned known method has the following disadvantages. That is, two steps are required in this method to obtain the intended compound from a 5-hydrazino-1H-pyrazol-4-carboxylate compound. Moreover, much time should be allowed to complete the ring closure reaction. Further, when the intended 1H-pyrazolo[5,1-c]-1,2,4-triazole compound has a substituent group reactive to phosphorous oxychloride, such as for example a carboxyl group or a hydroxyl group, the yield of the intended compound is considerably lowered. Furthermore, phosphorous compounds formed as a result of this reaction should be treated in order to avoid environmental pollution, and this treatment may be a heavy burden when commercially practicing the above method.

Another known method of preparing 1H-pyrazolo[5,1c]-1,2,4-triazole compounds is disclosed in JP-A-62-158283 (the term "JP-A" as used herein means an unexamined published Japanese Patent Application). This method comprises acylating a 5-hydrazino-1H-pyrazole compound to obtain a 5-acylhydrazino-1H-pyrazole compound, subsequently reacting the 5-acylhydrazino-1H-pyrazole compound with thionyl chloride, and then ring-closing the resulting compound in the presence of an alcohol to thereby obtain a 1H-pyrazolo[5,1-c]-1,2,4-triazole compound.

However, this method has similar disadvantages to those of the aforementioned method. For example, several steps are required for the reaction of this method, and when the intended 1H-pyrazolo[5,1,-c]-1,2,4-triazole compound has a substituent group reactive to thionyl chloride, such as for example a carboxyl group or a hydroxyl group, the yield of the intended compound is considerably lowered. Further, sulfur dioxide from this reaction needs to be treated so as to prevent environmental pollution, and this is a heavy burden when this method is commercially practiced.

Accordingly, it is an object of the present invention to provide a process for preparing 1H-pyrazolo[5,1-c]-1,2,4-triazole compounds from 5-hydrazino-1H-pyrazole compounds by a one-step reaction which is completed in a short time with high yields.

It is another object of the present invention to provide a process for preparing 1H-pyrazolo[5,1-c]-1,2,4-triazole compounds in high yields even when a substituent group reactive to phosphorous oxychloride, thionyl chloride or the like is present in the molecules of said compounds.

It is a further object of the present invention to provide a process for preparing 1H-pyrazolo[5,1-c]-1,2,4-triazole compounds without the formation of phosphorous compounds and sulfur dioxide, which are harmful substances from an environmental viewpoint.

SUMMARY OF THE INVENTION

These and other objects are achieved by the present invention providing a process for preparing a 1H-pyrazolo[5,1-c]-1,2,4-triazole compound represented by the following general formula (I):

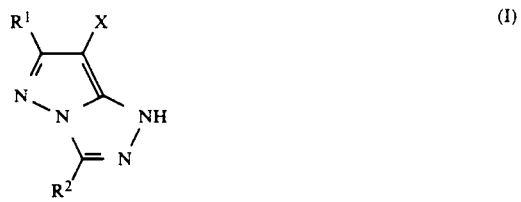

wherein $R^1$ represents a hydrogen atom or a substituent group, $R^2$ represents an alkyl group, an aryl group or a heterocyclic group, and X represents a hydrogen atom or a substituent group, which process comprises reacting either an imidic acid ester represented by the following general formula (II):

wherein $R^2$ is as defined above, $R^3$ represents an alkyl group, and Y represents an acid radical, or an orthoester represented by the following general formula (III):

wherein $R^2$ and $R^3$ are as defined above, with a 5-hydrazino-1H-pyrazole compound represented by the following general formula (IV):

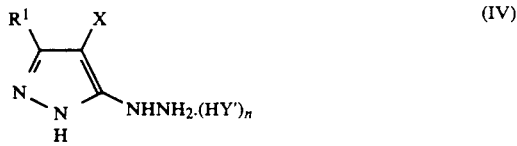

wherein $R^1$ and X are as defined above, Y' represents an acid radical, and n represent 0 or a positive integer necessary to neutralize the intramolecular electric charge.

DETAILED DESCRIPTION OF THE INVENTION

The reaction in the process of the present invention is thought to proceed according to the following reaction scheme (1):

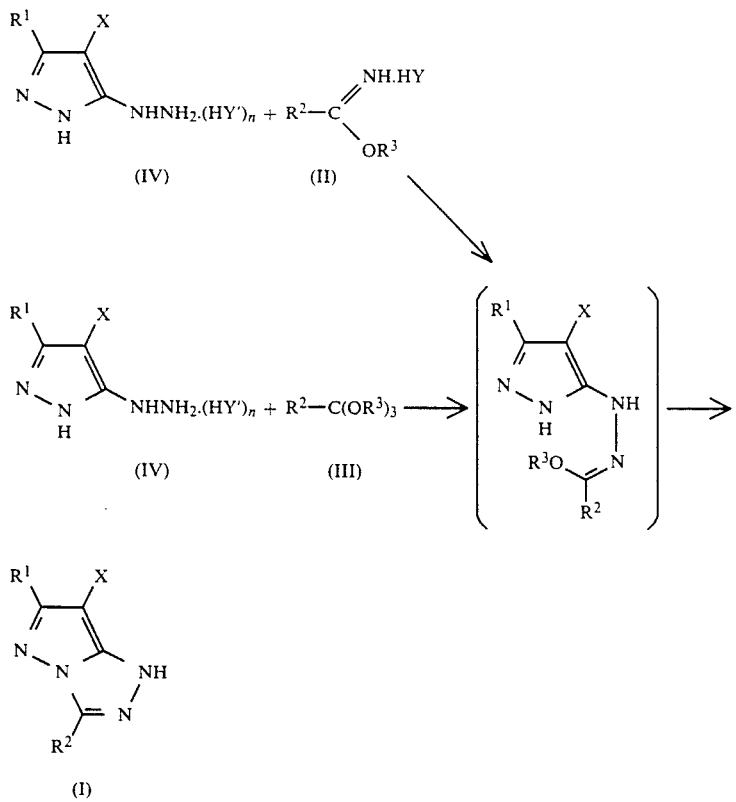

In general formula (IV) representing the 5-hydrazino-1H-pyrazole compound to be employed as a starting material in the present invention, X represents a hydrogen atom, or a halogen atom. Preferably, X represents a hydrogen atom, a halogen atom, a cyano group, a nitro group, an alkoxy group, a phenoxy group, a 2-benzimidazolyloxy group, an alkylthio group, a phenylthio group, an ester group or to the following formulas:

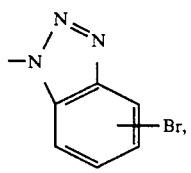

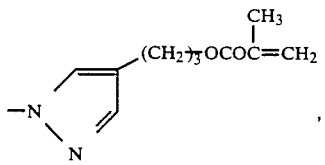

More specifically, X represents a hydrogen atom; a halogen atom (e.g., fluorine, chlorine), an alkoxy group (e.g., methoxy, ethoxy), an aryloxy group (e.g., phenoxy, p-cresyl, p-methoxyphenoxy), a heterocyclic oxy group (e.g., 2-benzimidazolyloxy), an alkylthio group (e.g., dodecylthio, 2-ethoxycarbonyltridecylthio, ethoxycarbonylmethylthio), an arylthio group (e.g., 4-dodecyloxyphenylthio, 2-butoxy-5-t-octylphenylthio), an ester group (e.g., methoxycarbonyl, ethoxycarbonyl), a cyano group, a nitro group or 3- to 10-membered heterocyclic group as illustrated below,

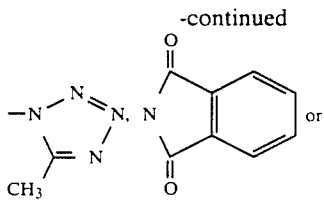

-continued

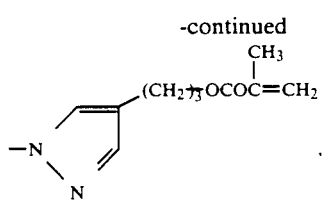

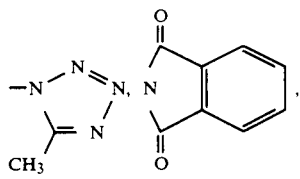

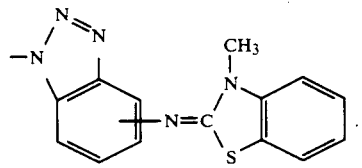

R¹ in general formula (IV) preferably represents a hydrogen atom; an alkyl group (e.g., methyl, ethyl, isopropyl, t-butyl), an phenyl group (e.g., phenyl, 2-methoxyphenyl), a cyano group, an alkoxy group (e.g., methoxy, ethoxy, 2-methoxyethoxy, 2-phenoxyethoxy, 2-methylsulfonylethoxy, 2,4-di-t-amylphenoxy), an phenoxy group (e.g., phenoxy, 4-methoxyphenoxy, 2-methoxyphenoxy, 2,4-dimethylphenoxy), an acylamino group (e.g., acetylamino, dodecanoylamino, benzoylamino), an anilino group (e.g., 2,5-dichloroanilino, p-nitroanilino), a ureido group (e.g., methylureido, phenylureido), a a urethane group, sulfamoylamino group, an alkylthio group (e.g., methylthio, octylthio), an phenylthio group (e.g., phenylthio, 4-nitrophenylthio), an alkoxycarbonylamino group (e.g., methoxycarbonylamino), a sulfonamido group (e.g., methanesulfonamido, dodecanesulfonamido, p-toluenesulfonamido), a carbamoyl group (e.g., N-butylcarbamoyl, N,N-diethylcarbamoyl), a sulfamoyl group (e.g., N-butylsulfamoyl, N-cyclohexylsulfamoyl, N,N-dibutylsulfamoyl), a sulfonyl group (e.g., methylsulfonyl, ethylsulfonyl), or an alkoxycarbonyl group (e.g., methoxycarbonyl, ethoxycarbonyl).

Y' represents an acid radical which may be inorganic or organic. Examples of the inorganic acid radical include acid radicals of hydrochloric acid, sulfuric acid and the like. Examples of the organic acid radical include acid radicals of methanesulfonic acid, p-toluenesulfonic acid and the like. The symbol n represents an integer of 0 to 2, preferably 0 or 1.

Specific examples of the compound represented by general formula (IV) are shown below, but they are not to be construed as limiting the scope of the invention.

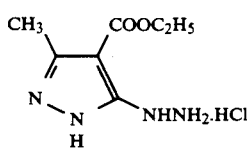

IV-1

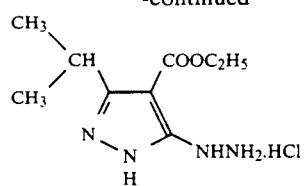

IV-2

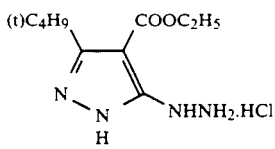

IV-3

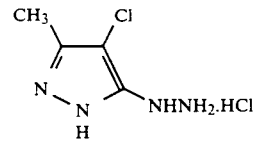

IV-4

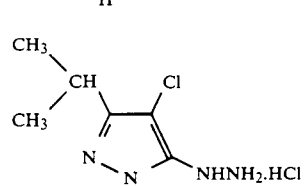

IV-5

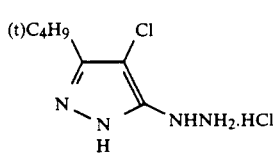

IV-6

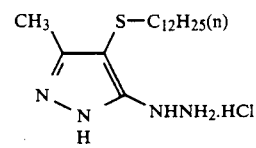

IV-7

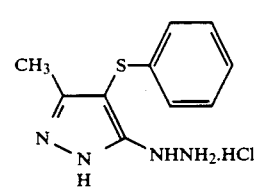

IV-8

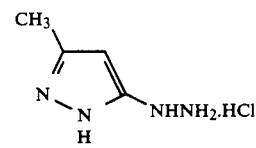

IV-9

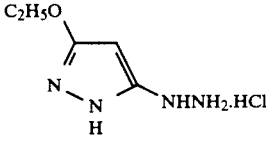

IV-10

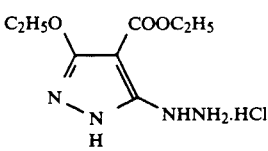

IV-11

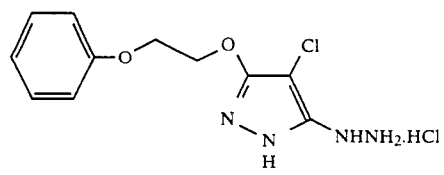

IV-12

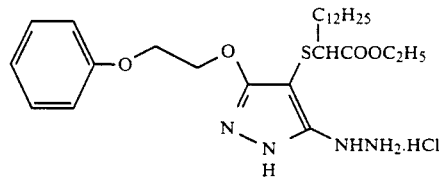

IV-13

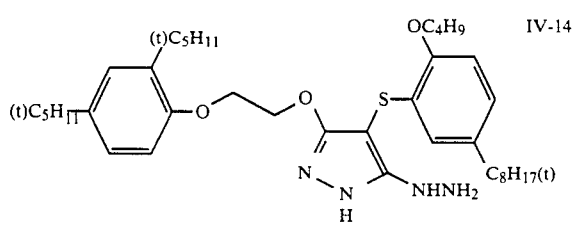

IV-14

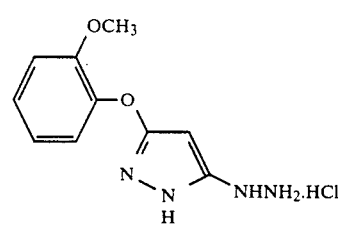

IV-15

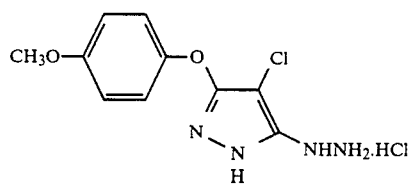

IV-16

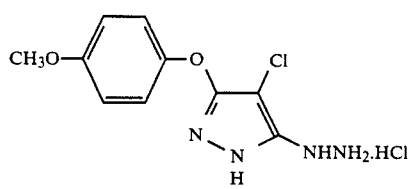

IV-16

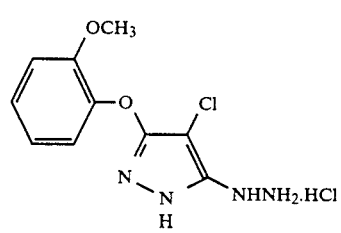

IV-17

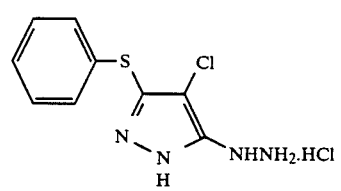

IV-18

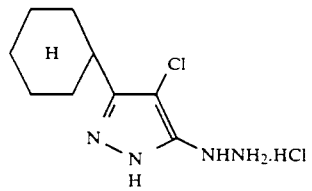

IV-19

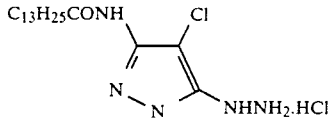

IV-20

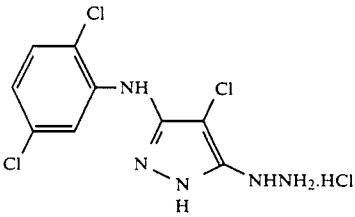

IV-21

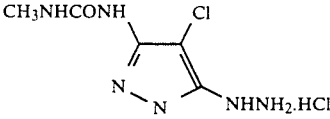

IV-22

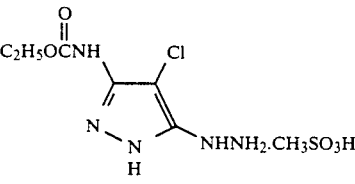

IV-23

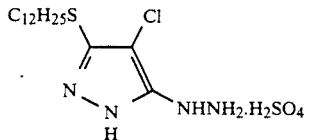

IV-24

In general formula (II) representing the imidic acid ester and in general formula (III) representing the orthoester, $R^2$ represents an alkyl group, an aryl group or a heterocyclic group. Preferably, $R^2$ represents an alkyl group having 1 to 30 carbon atoms an aryl group having 6 to 30 carbon atoms (e.g., phenyl, naphthyl), 4-pyridyl group or a 3-pyridyl group group containing $R^3$ represents a an alkyl group having 1 to 20 carbon atoms. Preferably, $R^3$ is an alkyl group having 1 to 10 carbon atoms. Y has the same meaning as Y' defined above.

The starting material to be employed in the present invention, the 5-hydrazino-1H-pyrazole compound represented by general formula (IV), can be prepared by diazotizing the corresponding 5-amino-1H-pyrazole compound and then reducing the resulting diazo-compound, according to conventional methods. For example, a 5-hydrazino-1H-pyrazole compound can be synthesized by the method described in "Organic Syntheses Collective Volume", vol. 1, p. 422, or "Journal of the Chemical Society", p. 167 (1971).

The imidic acid ester represented by general formula (II) can be prepared according to Pinner's method, that is, by the addition of an alcohol or phenol to the nitril corresponding to the intended imidic acid ester, in the presence of an acid.

The orthoester represented by general formula (III) can be prepared by, for example, the method described in "Shin Jikken Kagaku Kouza (Course of New Experimental Chemistry", vol. 14, p. 1099 (1977). That is, an orthoester can be obtained by reacting the imidic acid ester prepared by Pinner's method mentioned above with an excess of alcohol.

Specific examples of the compound represented by general formula (II) are shown below, but they are not to be construed as limiting the scope of the invention.

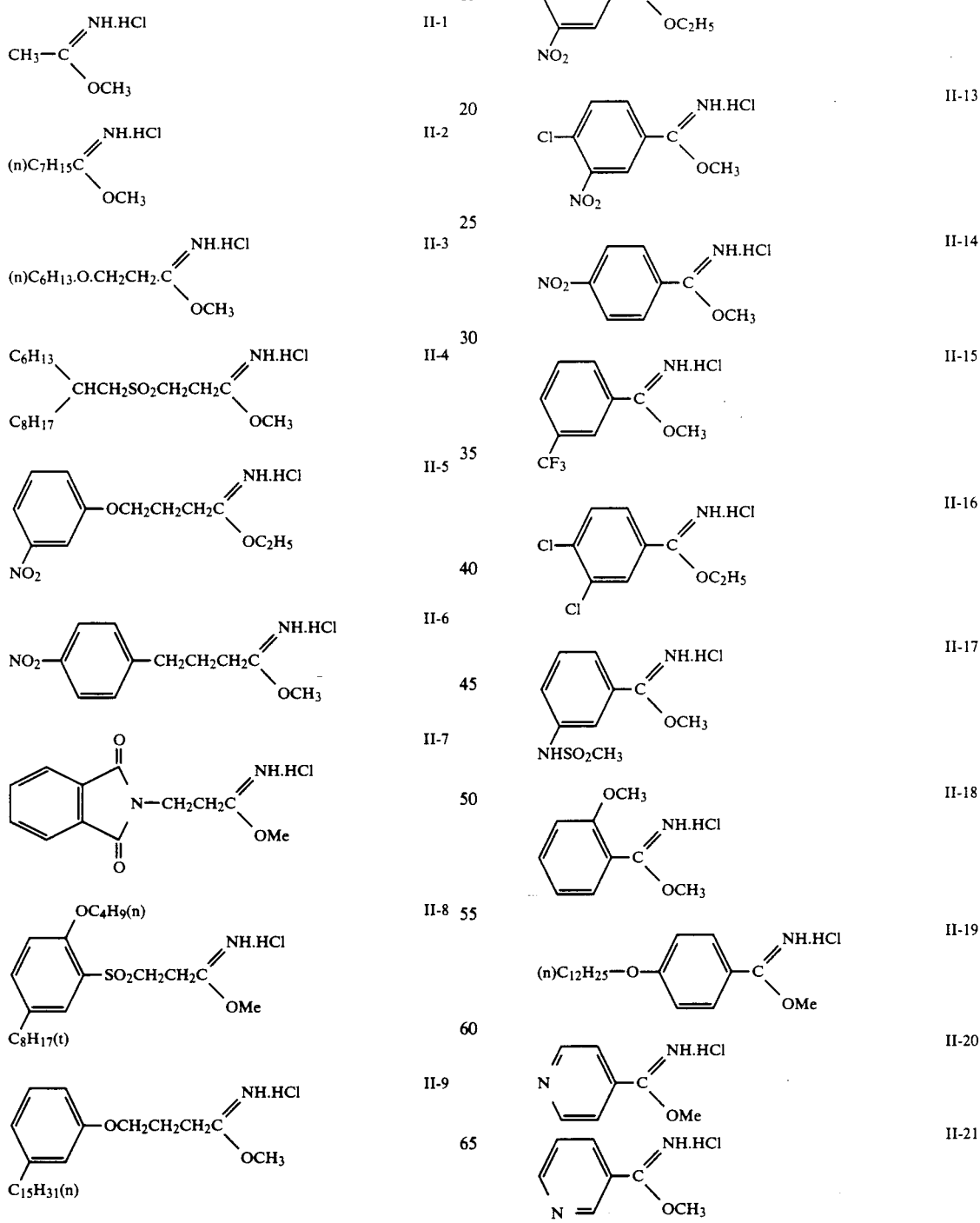

-continued

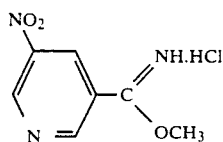

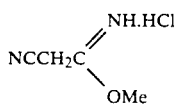

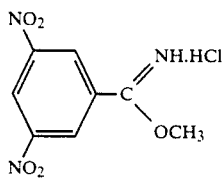

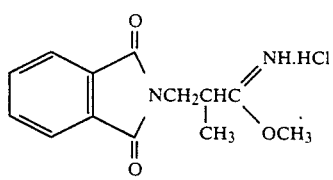

Specific examples of the compound represented by general formula (III) are shown below, but they are not to be construed as limiting the scope of the invention.

CH$_3$.C.(OC$_2$H$_5$)$_3$   III-1

C$_3$H$_7$.C.(OCH$_3$)$_3$   III-2

NC—CH$_2$—C(OCH$_3$)$_3$   III-3

NC.CH$_2$(CH$_2$C(OC$_2$H$_5$)$_3$   III-4

III-5

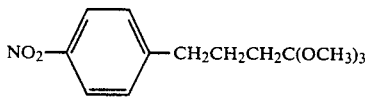

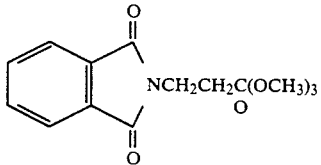   III-6

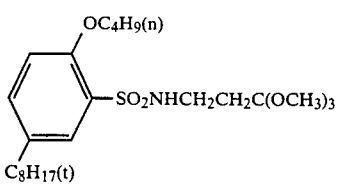   III-7

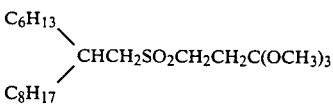   III-8

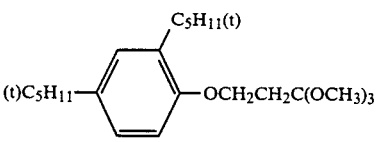   III-9

-continued

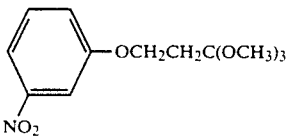   III-10

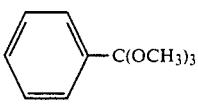   III-11

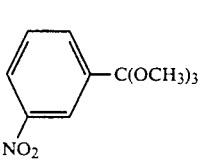   II-12

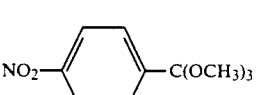   III-13

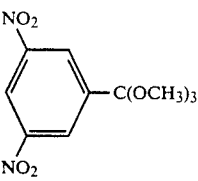   III-14

III-15

The embodiments of the present invention will now be explained hereinbelow.

The reaction of the imidic acid ester represented by general formula (II) with the 5-hydrazino-1H-pyrazole compound represented by general formula (IV) and the reaction of the orthoester represented by general formula (III) with the 5-hydrazino-1H-pyrazole compound represented by general formula (IV) may, in either case, be performed without a medium or by using a suitable solvent with the reactants dissolved or dispersed therein. Representative examples of the solvent which can be suitably employed in the present invention include dimethyl sulfoxide, sulfolane, dimethylacetamide, benzene, toluene, 1,2-dimethoxyethane, and alcohols such as methanol, ethanol, isopropyl alcohol, t-butyl alcohol and the like. These solvents may be used alone or in combination of two or more thereof.

The amount of the solvent may be 1 to 100 parts by weight, preferably 1 to 10 parts by weight per part by weight of the compound represented by general formula (IV).

The molar ratio of the compound represented by general formula (IV) to the compound represented by general formula (II) or to the compound represented by general formula (III) may be in the range of from 1:1 to 1:10. In the case when the reaction is conducted without a solvent, the preferred range of the molar ratio is 1:1 to 1:10. In the case when the reaction is conducted using a suitable solvent such as those mentioned above, the molar ratio is preferably in the range of from 1:1 to 1:5.

In practicing the present invention, the compound represented by the general formula (IV) may be used in the form of an acid salt. However, it is preferred that an organic base such as pyridine and triethylamine or an inorganic weak base such as sodium hydrogencarbonate, potassium carbonate, and sodium acetate be introduced into the reaction system beforehand to convert the compound of formula (IV) in the form of an acid salt into the acidfree form, before the reaction is performed. Such a base may be used in an amount of 1 to 10 moles, preferably 1 to 3 moles per mole of the compound represented by general formula (IV).

The reaction temperature is preferably in the range of from 50° to 200° C. and is particularly preferable in the range of from 60° to 150° C.

The time required to complete the reaction may be 1 to 10 hours if the reaction temperature is within the preferred range, 50° to 200° C.

Under the conditions explained above, the compound of formula (IV) is allowed to react with the compound of formula (II) or with the compound of formula (III) to thereby obtain a 1H-pyrazolo[5,1-c]-1,2,4-triazole compound represented by the following general formula (I):

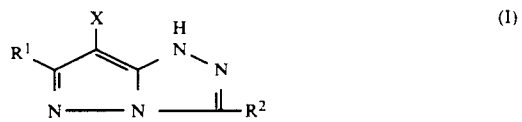

wherein $R^1$, X and $R^2$ are as defined hereinbefore with respect to the general formulae (IV), (II), and (III).

Specific examples of the 1H-pyrazolo[5,1-c]-1,2,4-triazole compound represented by general formula (I) are shown below, but they are not to be construed as limiting the scope of the invention.

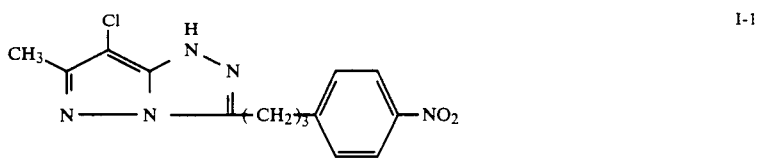

I-1

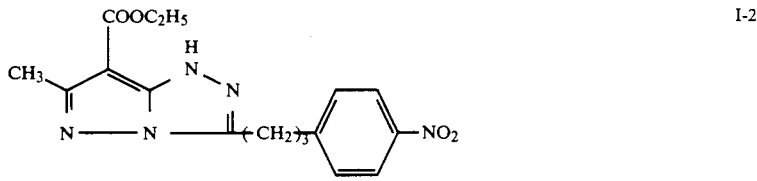

I-2

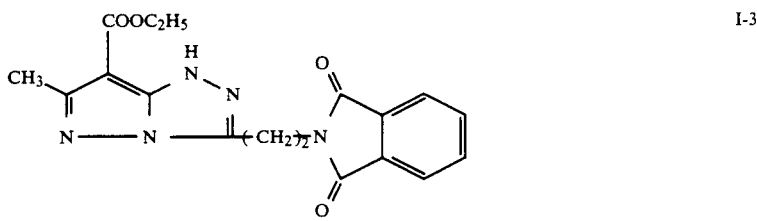

I-3

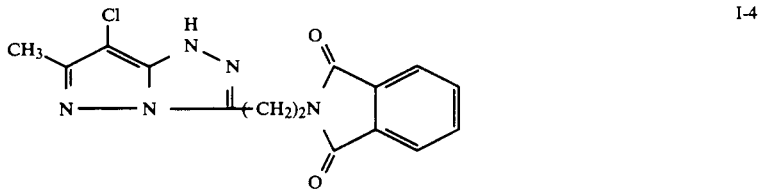

I-4

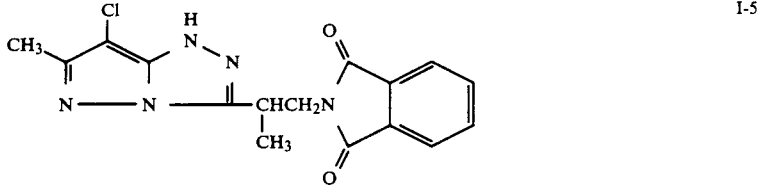

I-5

-continued
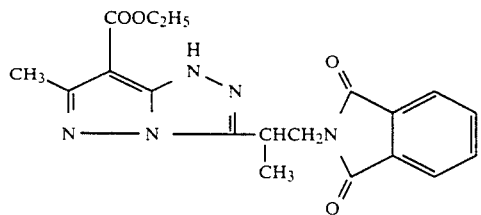 I-6
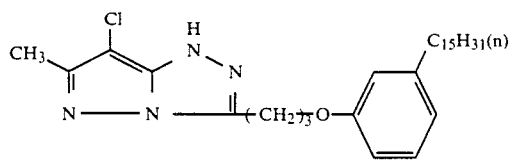 I-7
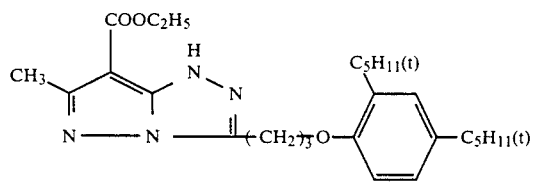 I-8
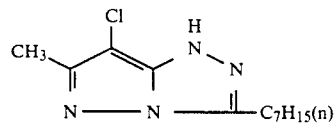 I-9
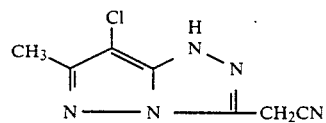 I-10
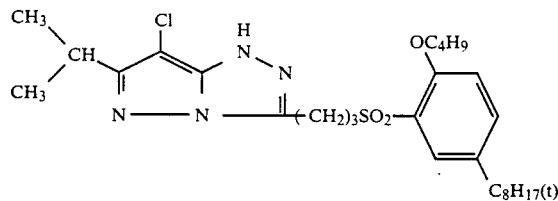 I-11
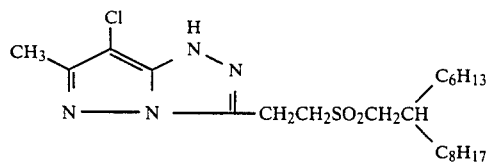 I-12
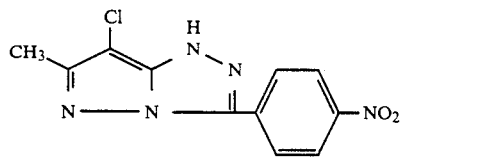 I-13
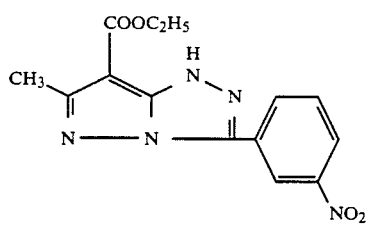 I-14

-continued
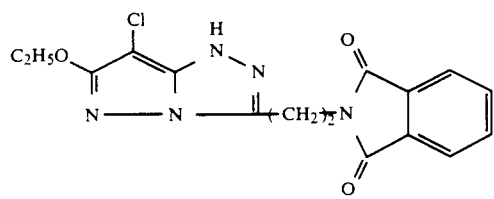 I-15
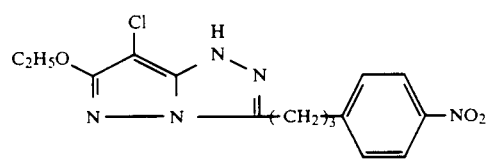 I-16
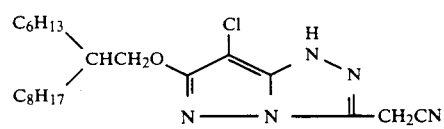 I-17
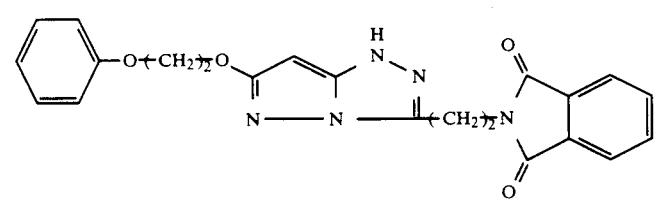 I-18
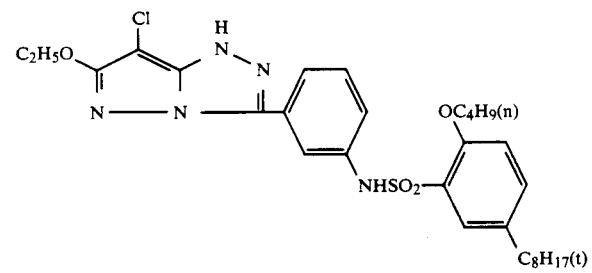 I-19
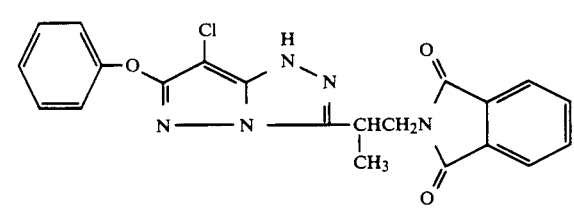 I-20
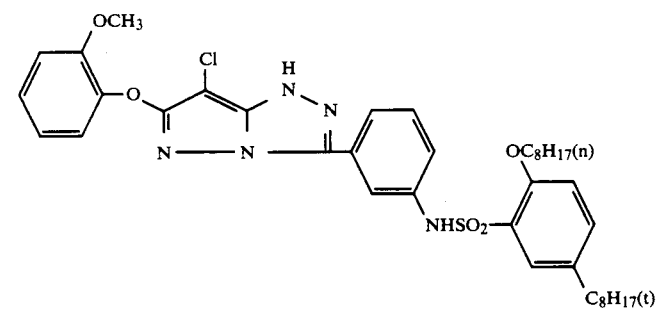 I-21

-continued

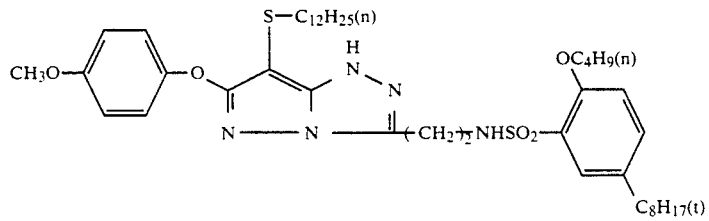
I-22

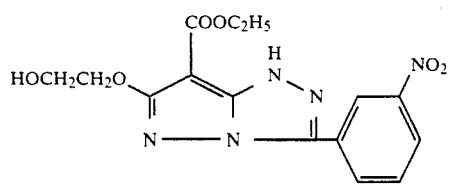
I-23

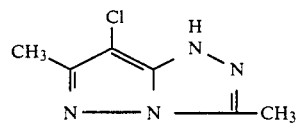
I-24

According to the process of the present invention, 1H-pyrazolo[5,1-c]-1,2,4-triazole compounds can be synthesized in high yields through a simple one-step reaction, as described above, without the formation of harmful byproducts which may cause environmental pollution.

This invention will now be described in more detail with reference to the following Examples but the Examples should not be construed to limit the scope of the present invention.

EXAMPLE 1

Preparation of Compound I-2 as shown before

To 75 ml of toluene is added 8.8 g of Compound IV-1 as shown before and 12.9 g of Compound III-5 as shown before. The resulting mixture is heated, with stirring, for about 3 hours on an oil bath at a temperature of 130° C. After completion of the reaction, the reaction mixture is cooled to room temperature, and then poured into an aqueous sodium hydrogencarbonate solution, whereby an oily substance is separated. This oily substance is extracted with ethyl acetate. The resulting ethyl acetate layer is dried over anhydrous magnesium sulfate, and then the ethyl acetate is distilled off under reduced pressure to obtain a residue. The residue is recrystalized from acetonitrile, thereby obtaining 8.1 g of Compound I-2 in a yield of 56.5%. The analytical data for this compound are shown in Table (I) below.

EXAMPLE 2

Preparation of Compound I-6 as shown before

To 6.78 g of Compound II-25 as shown before is added 30 ml of methanol and the resulting mixture is stirred at room temperature for one hour. Thereafter, 4.40 g of Compound IV-1 as shown before is added thereto, and the resulting mixture is heated under reflux for 7 hours. Then, the reaction mixture is cooled, whereby a crystalline precipitate separates out. This precipitate is recrystalized from ethanol to obtain 3.34 g of Compound I-6 in a yield of 43.8%. The analytical data for this compound are shown in Table I below.

Further, in substantially the same manner as in Example 2, Compounds I-7, I-8, I-9, I-11 and I-12, as shown before, are synthesized. The analytical data for these compounds are also shown in Table (I) below.

TABLE I

| Compound No. | $R^1$ | $R^2$ | X | Synthesis method | Yield (%) | Melting point (°C.) | $^1$H-NMR Spectral Data (δ; ppm) |
|---|---|---|---|---|---|---|---|
| I-2 | CH$_3$— | –(CH$_2$)$_3$–C$_6$H$_4$–NO$_2$ | —COOC$_2$H$_5$ | Example 1 | 56.5 | 120~128 | CDCl$_3$, 9.43(1H, s), 8.10(2H, d), 7.31(2H, d), 4.33(2H, q), 3.2~1.7 (9H, m), 1.40(3H, t) |
| I-6 | " | —CHCH$_2$N(phthalimide)  \|  CH$_3$ | " | Example 2 | 43.8 | — | CDCl$_3$, 7.74(4H, m), 4.27(2H, q), 4.2~3.5(3H, m), 2.23(3H, s), 1.53(3H, d), 1.33(3H, t) |

TABLE I-continued

R¹-C(X)=... (structure header)

| Compound No. | R¹ | R² | X | Synthesis method | Yield (%) | Melting point (°C.) | ¹H-NMR Spectral Data (δ; ppm) |
|---|---|---|---|---|---|---|---|
| I-7 | " | –(CH₂)₃O–C₆H₄–C₁₅H₃₁(n) | —Cl | same as Example 2 | 53.3 | 98~99 | CDCl₃, 10.0(1H, s), 7.2~6.5(4H, m), 0.86(3H, t), 4.05(2H, t), 3.13(2H, t), 2.67~2.2(7H, m), 1.67~1.1(29H, m) |
| I-8 | " | (CH₂)₃O–C₆H₃(C₅H₁₁(t))(C₅H₁₁(t)) | —COOC₂H₅ | same as Example 2 | 48.5 | oily substance | CDCl₃, 7.3~6.67(3H, m), 4.38(2H, q), 4.10(2H, t), 3.24(2H, t), 2.60(3H, s), 2.34(2H, qui), 2.0~0.5(25H, m) |
| I-9 | " | —C₇H₁₅(n) | —Cl | same as Example 2 | 45.5 | 92.6 | — |
| I-11 | (CH₃)₂CH— | (CH₂)₃SO₂–C₆H₃(OC₄H₉(n))(C₈H₁₇(t)) | " | same as Example 2 | 38.7 | 120~122 | CDCl₃, 9.46(1H, br), 7.97(1H, br), 7.56(1H, d), 7.30(1H, s), 6.93(1H, d), 4.07(2H, t), 3.56(2H, t), 3.05(3H, m), 2.5~2.1(2H, m), 1.8~0.8(21H, m), 0.7(9H, s) |
| I-12 | CH₃— | —CH₂CH₂SO₂CH₂CH(C₆H₁₃)(C₈H₁₇) | " | same as Example 2 | 44.5 | 55~60 | CDCl₃, 10.60(1H, s), 3.54(4H, m), 2.95(2H, d), 2.33(3H, s), 2.12(1H, m), 1.67~1.07(24H, br), 0.84(6H, t) |

While the invention has been described in detail and with reference to specific embodiments thereof, it will be apparent to one skilled in the art that various changes and modifications can be made therein without departing from the spirit and scope thereof.

What is claimed is:

1. A process for preparing a [1H-pyrazolo[5,1-c]-1,2,4-triazole] 1H-pyrazolo(5,1-c)-1,2,4-triazole compound represented by formula (I):

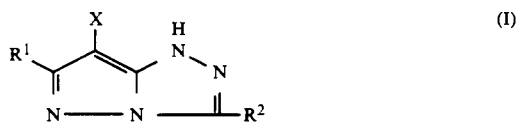

(I)

wherein

R¹ represents a hydrogen atom, an alkyl group, a phenyl group, a cyano group, an alkoxy group, a phenoxy group, 4-methoxyphenoxy, 2-methoxyphenoxy, 2,4-dimethylphenoxy, an acylamino group, an anilino group, a ureido group, a urethane group, a sulfamoylamino group, an alkylthio group, a phenylthio group, an alkoxycarbonylamino group, a sulfonamido group, a carbamoyl group, a sulfamoyl group, a sulfonyl group or an alkoxycarbonyl group, R² represents an alkyl group, an aryl group having 6 to 30 carbon atoms, a 4-pyridyl group, or a 3-pyridyl group, and X represents a hydrogen atom, a halogen atom, a cyano group, a nitro group, an alkoxy group, a phenoxy group, 4-methoxyphenoxy, 2-methoxyphenoxy, 2,4-dimethylphenoxy, 2-benzimidazolyloxy group, an alkylthio group, a phenylthio group, an alkoxycarbonyl group,

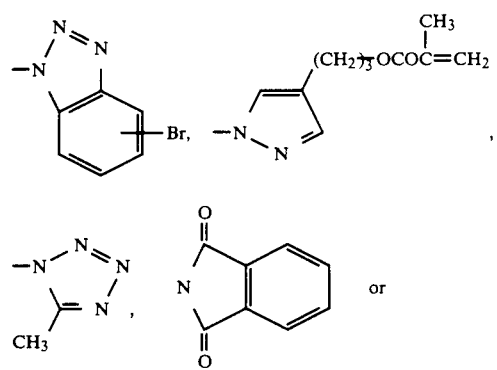

-continued

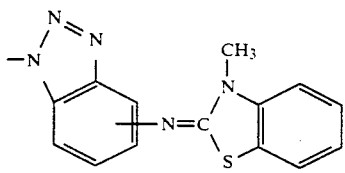

which process comprises reacting an imidic acid ester represented by formula (II):

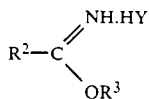
(II)

wherein $R^2$ is as defined above, $R^3$ represents an alkyl group, and Y represents an acid radical of hydrochloric acid, sulfuric acid, methanesulfonic acid or p-toluenesulfonic acid, with a 5-hydrazino-1H-pyrazole compound represented by formula (IV):

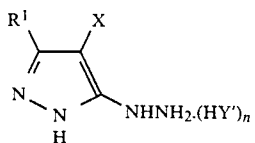
(IV)

wherein $R^1$ and X are as defined above, Y' represents an acid radical of hydrochloric acid, sulfuric acid, methanesulfonic acid or p-toluenesulfonic acid, and n represents 0, 1 or 2.

2. The process according to claim 1, wherein X is an alkoxycarbonyl group selected from the group consisting of a methoxycarbonyl group and an ethoxycarbonyl group.

3. The process according to claim 1, wherein the compounds represented by formula (II) are selected from the group consisting of formulas (II-11)-(II-19) and (II-24):

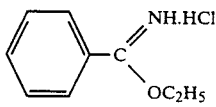 II-11

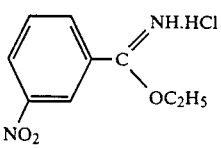 II-12

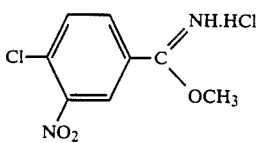 II-13

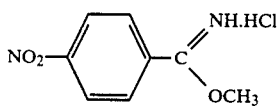 II-14

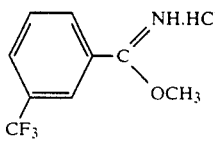 II-15

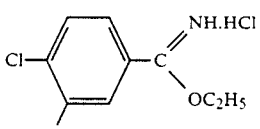 II-16

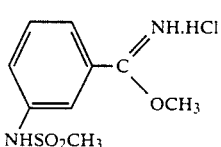 II-17

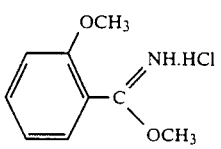 II-18

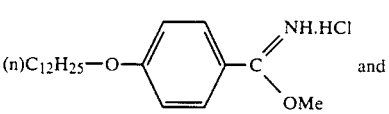 II-19 and

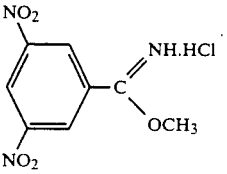 II-24

4. The process according to claim 1, wherein Y' is an acid radical of hydrochloric acid or sulfuric acid.

5. The process according to claim 4, wherein Y' is an acid radical of hydrochloric acid.

6. The process according to claim 1, wherein n is 0 or 1.

7. The process according to claim 1, wherein $R^2$ represents an alkyl group having 1 to 30 carbon atoms which may be straight chain, branched or cyclic, or a phenyl group or a naphthyl group.

8. The process according to claim 1, wherein the reaction of the imidic acid ester represented by formula (II) with the 5-hydrazino-1H-pyrazole compound represented by formula (IV) and the reaction of the orthoester represented by formula (III) with the 5-hydrazino-1H-pyrazole compound represented by formula (IV) is performed in a solvent with the reactants dissolved or dispersed therein.

9. The process according to claim 8, wherein the solvent is selected from at least one member of the group consisting of dimethyl sulfoxide, sulfolane, dimethylacetamide, benzene, toluene, 1,2-dimethoxyethane, and alcohols.

10. The process according to claim 8, wherein the amount of the solvent is 1 to 100 parts by weight per part by weight of the compound represented by formula (IV).

11. The process according to claim 1, wherein the molar ratio of the compound represented by formula (IV) to the compound represented by formula (II) or to the compound represented by formula (III) is in the range of from 1:1 to 1:10.

12. The process according to claim 11, wherein the molar ratio is in the range of from 1:1 to 1:5.

13. The process according to claim 1, wherein the compound represented by formula (IV) is in the form of an acid salt.

14. The process according to claim 1, wherein the compound represented by formula (IV) is in the acid-free form.

15. The process according to claim 1, wherein the reaction temperature is in the range of from 50° to 200° C.

16. The process according to claim 15, wherein the reaction time is 1 to 10 hours.

17. The process according to claim 1, wherein $R^1$ represents an alkyl group, an alkoxy group, a phenoxy group, an alkylthio group, a phenylthio group, an acylamino group, a ureido group, an anilino group or a urethane group.

18. The process according to claim 1, wherein X represents a hydrogen atom, a halogen atom, an alkoxycarbonyl group, an alkylthio group or a phenylthio group.

19. The process according to claim 1, wherein $R^2$ represents an alkyl group or a phenyl group.

* * * * *